(12) United States Patent
Parker

(10) Patent No.: US 8,708,997 B2
(45) Date of Patent: Apr. 29, 2014

(54) INTRODUCER SHEATH

(75) Inventor: Fred T. Parker, Unionville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 558 days.

(21) Appl. No.: 13/009,454

(22) Filed: Jan. 19, 2011

(65) Prior Publication Data
US 2011/0257599 A1   Oct. 20, 2011

Related U.S. Application Data

(63) Continuation of application No. 09/815,567, filed on Mar. 23, 2001.

(60) Provisional application No. 60/191,709, filed on Mar. 23, 2000.

(51) Int. Cl.
*A61M 25/00* (2006.01)
(52) U.S. Cl.
USPC ........................................... 604/526
(58) Field of Classification Search
USPC ......... 604/93.01, 103.09, 264, 523–527, 529; 600/585
See application file for complete search history.

(56) References Cited

U.S. PATENT DOCUMENTS

| | | | |
|---|---|---|---|
| 4,276,250 A | 6/1981 | Satchell et al. | 264/167 |
| 4,385,635 A | 5/1983 | Ruiz | 128/658 |
| 4,563,181 A | 1/1986 | Wijayarathna et al. | 604/280 |
| 4,636,346 A | 1/1987 | Gold et al. | 264/139 |
| 4,657,024 A | 4/1987 | Coneys | 128/658 |
| 4,739,768 A | 4/1988 | Engelson | 128/658 |
| 4,775,371 A | 10/1988 | Mueller, Jr. | 604/280 |
| 4,898,591 A | 2/1990 | Jang et al. | 604/282 |
| 5,017,259 A | 5/1991 | Kohsai | 156/294 |
| 5,045,072 A | 9/1991 | Castillo et al. | 604/280 |
| 5,066,285 A | 11/1991 | Hillstead | 604/164 |
| 5,085,649 A | 2/1992 | Flynn | 604/282 |
| 5,147,332 A | 9/1992 | Moorehead | 604/247 |
| 5,171,232 A | 12/1992 | Castillo et al. | 604/280 |
| 5,180,376 A | 1/1993 | Fischell | 604/282 |
| 5,221,270 A | 6/1993 | Parker | 604/282 |
| 5,222,949 A | 6/1993 | Kaldany | 604/282 |
| 5,234,416 A | 8/1993 | Macaulay et al. | 604/282 |
| 5,258,160 A | 11/1993 | Utsumi et al. | 264/558 |
| 5,300,048 A | 4/1994 | Drewes, Jr. et al. | 604/280 |

(Continued)

OTHER PUBLICATIONS

Check-Flo® Performer Introducer Sets; Cook Incorporated Catalog; Copyright 1997.

*Primary Examiner* — Anu Ramana
(74) *Attorney, Agent, or Firm* — Brinks Gilson & Lione

(57) ABSTRACT

Introducer sheath (10,30,40) having a flexible kink-resistant distal tip portion (26,32,42). A multilayer sheath structure is used, with an inner tube (12) such as PTFE having a coil (14) of wire wound therearound. A first length of outer tubing (20) such as of nylon is inserted over most of the coil-wound inner tube (12) in a manner exposing a distal length of coil-wound inner tube. A second length of outer tubing (22) with a softer durometer than first outer tubing length (20), is inserted over the exposed coil-wound inner tube and extends for a slight distance beyond the end of the coil. During heat application, the outer tubing lengths (20,22) are melted to bond to each other and to flow between the spacings of the coil turns to bond to the roughened outer surface of the inner tube (12). The distal tip region corresponding to the second tubing length is flexible and is kink-resistant due to the coil (14).

20 Claims, 3 Drawing Sheets

(56) References Cited

U.S. PATENT DOCUMENTS

| | | | |
|---|---|---|---|
| 5,342,299 A | 8/1994 | Snoke et al. | 604/95 |
| 5,354,257 A | 10/1994 | Roubin et al. | 600/7 |
| 5,368,564 A | 11/1994 | Savage | 604/95 |
| 5,380,304 A | 1/1995 | Parker | 604/282 |
| 5,399,164 A | 3/1995 | Snoke et al. | 604/95 |
| 5,423,764 A | 6/1995 | Fry | 604/187 |
| 5,454,795 A | 10/1995 | Samson | 604/282 |
| 5,456,674 A | 10/1995 | Bos et al. | 604/280 |
| 5,498,250 A | 3/1996 | Prather | 604/280 |
| 5,499,975 A | 3/1996 | Cope et al. | 604/165 |
| 5,507,725 A | 4/1996 | Savage et al. | 604/95 |
| 5,533,985 A | 7/1996 | Wang | 604/264 |
| 5,542,924 A | 8/1996 | Snoke et al. | 604/95 |
| 5,542,937 A | 8/1996 | Chee et al. | 604/280 |
| 5,554,139 A | 9/1996 | Okajima | 604/282 |
| 5,569,218 A | 10/1996 | Berg | 604/282 |
| 5,584,821 A | 12/1996 | Hobbs et al. | 604/280 |
| 5,599,305 A | 2/1997 | Hermann et al. | 604/95 |
| 5,599,325 A | 2/1997 | Ju et al. | 604/282 |
| 5,622,665 A | 4/1997 | Wang | 264/150 |
| 5,624,397 A | 4/1997 | Snoke et al. | 604/95 |
| 5,695,482 A | 12/1997 | Kaldany | 604/280 |
| 5,700,253 A | 12/1997 | Parker | 604/282 |
| 5,769,830 A | 6/1998 | Parker | 604/282 |
| 5,772,641 A | 6/1998 | Wilson | 604/280 |
| 5,792,124 A | 8/1998 | Horrigan et al. | 604/282 |
| 5,836,925 A | 11/1998 | Soltesz | 604/280 |
| 5,843,031 A | 12/1998 | Hermann et al. | 604/95 |
| 5,879,499 A | 3/1999 | Corvi | 156/175 |
| 5,891,110 A | 4/1999 | Larson et al. | 604/280 |
| 5,906,605 A | 5/1999 | Coxum | 604/525 |
| 5,908,413 A | 6/1999 | Lange et al. | 604/529 |
| 5,911,715 A | 6/1999 | Berg et al. | 604/525 |
| 5,944,738 A | 8/1999 | Amplatz et al. | 606/213 |
| 5,947,940 A | 9/1999 | Beisel | 604/282 |
| 5,948,489 A | 9/1999 | Hopkins | 428/34.9 |
| 5,951,929 A | 9/1999 | Wilson | 264/139 |
| 6,036,682 A | 3/2000 | Lange et al. | 604/529 |
| 6,048,485 A | 4/2000 | Field et al. | 264/322 |
| 6,143,013 A | 11/2000 | Samson et al. | 606/192 |
| 6,159,187 A | 12/2000 | Park et al. | 604/264 |
| 6,171,295 B1 | 1/2001 | Garabedian et al. | 604/524 |
| 6,174,330 B1 | 1/2001 | Stinson | 623/1.34 |
| 6,197,014 B1 | 3/2001 | Samson et al. | 604/524 |
| 6,210,396 B1 | 4/2001 | MacDonald et al. | 604/529 |

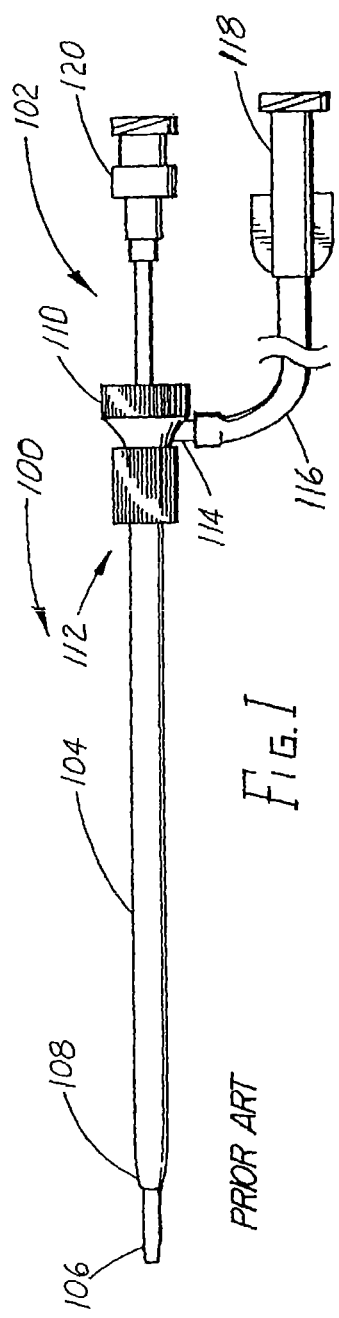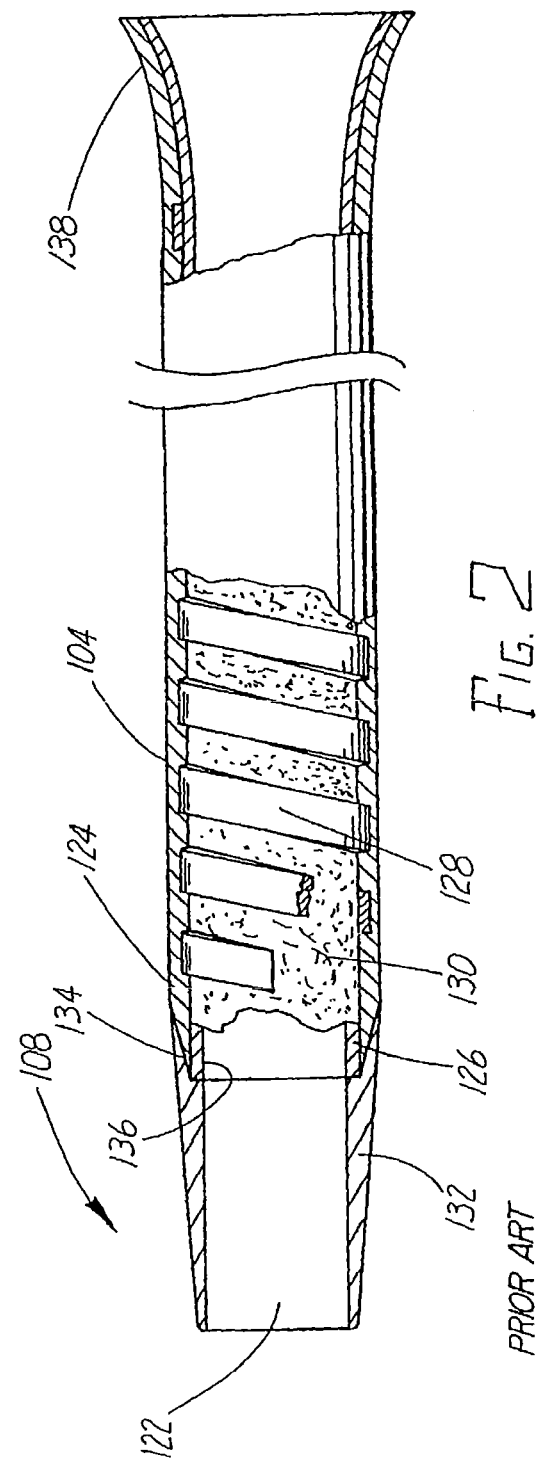

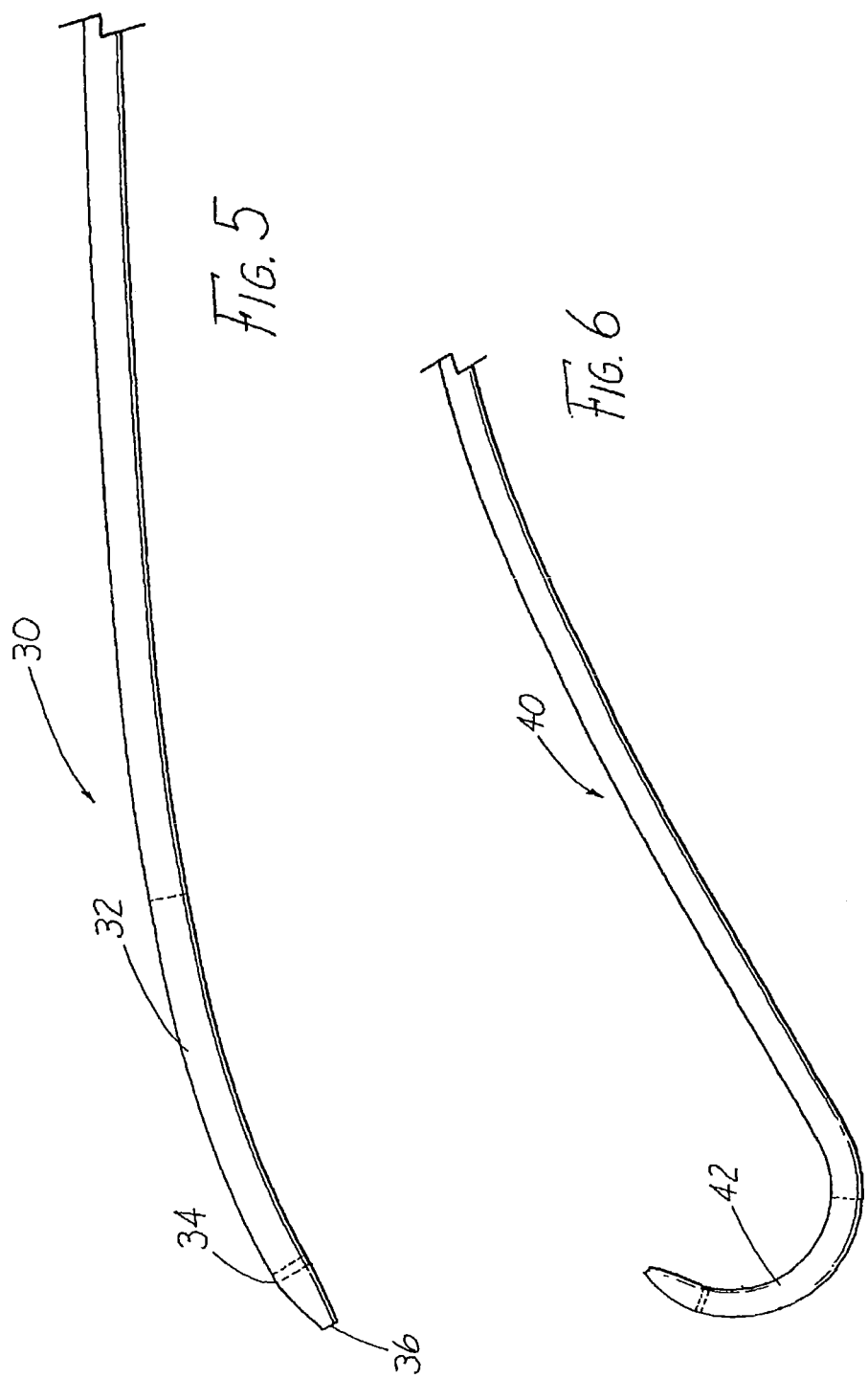

INTRODUCER SHEATH

RELATED APPLICATION INFORMATION

This application claims priority from U.S. Provisional Patent Application Ser. No. 60/191,709 filed Mar. 23, 2000.

FIELD OF THE INVENTION

The present invention relates to the field of medical devices and more particularly to introducer sheaths.

BACKGROUND OF THE INVENTION

Introducer sheaths are well-known for percutaneous vascular access and typically comprise polytetrafluoroethylene or fluorinated ethylene propylene. These sheaths are of a thin-walled construction, but tend to kink, which is unacceptable since upon kinking the sheath is unusable and cannot be straightened while positioned in the body of a patient and must therefore be removed leaving an enlarged, bleeding opening which typically cannot be reused for the necessary percutaneous entry. Increasing the thickness of the sheath wall only minimally improves the level of kink resistance while enlarging the entry hole which generally is undesirable.

One introducer sheath with improved kink resistance is disclosed in U.S. Pat. No. 5,380,304 to Parker. The introducer sheath comprises a coil having a plurality of turns positioned and compression-fitted around an inner tube. An outer tube is connected to the inner tube through the uniform spacing of the coil turns. As a result, the compression-fitted coil reinforces the wall to provide an extremely kink-resistant and thin-walled introducer sheath. Preferably, the coil comprises flat wire for minimizing the wall thickness of the sheath.

The distal ends of the inner and outer tubes extend beyond the distal end of the coil, and the distal end of the outer tube is tapered and extends beyond the distal end of the inner tube to advantageously prevent the inner tube from presenting a rough edge or surface, which may cause injury to the vessel wall. The outer tube is said to comprise a heat-formable polyamide material such as nylon for connecting with the rough outer surface of the inner tube, between the coil turns. A distal tip member of nylon is then bonded onto the distal tip of the outer tube, and is of the same durometer, or is harder to further facilitate entry into the percutaneous access site.

It is desired to provide a kink-resistant introducer sheath that has a more flexible distal tip, enabling introducer sheaths to be utilized in applications involving more tortuous paths or more sensitive treatment sites.

SUMMARY OF THE INVENTION

The foregoing problems are solved and a technical advance is achieved in an illustrative flexible, kink-resistant, introducer sheath having a flexible distal tip portion. The sheath of the present invention includes an inner tube such as of polytetrafluoroethylene, and a flat wire coil wound therearound. A first length of outer tubing of a conventional relatively hard material such as of nylon, extends along most of the length of the coil-wound inner tube. A second, short length of outer tubing is selected to have a softer durometer than the first length of outer tubing, and is placed over the exposed coil-wound length of the inner tube and abutted against the end of the first length of outer tubing. Both first and second lengths of outer tubing are melted to flow between the spacings of the coil wire to bond to the roughened outer surface of the inner tube and to thermally bond to each other at the abutment location. After appropriate tapering of the distal end of the second outer tubing length, a sheath is fabricated having a flexible distal tip portion.

Thus, the present invention provides an introducer sheath for use in applications such as renal and other arterial applications involving tortuous vascular paths and that has an atraumatic flexible kink-resistant distal tip portion.

BRIEF DESCRIPTION OF THE DRAWINGS

Embodiments of the present invention will now be described by way of example with reference to the accompanying drawings, in which:

FIG. 1 is a Prior Art elevation view of an introducer sheath assembly;

FIG. 2 is an enlarged partial cross-sectional view of the distal tip region of the Prior Art introducer sheath of FIG. 1;

FIGS. 5 and 6 illustrate sheaths of the present invention with distal tip regions that are either linear or formed to be arcuate.

DETAILED DESCRIPTION

Figure 3:
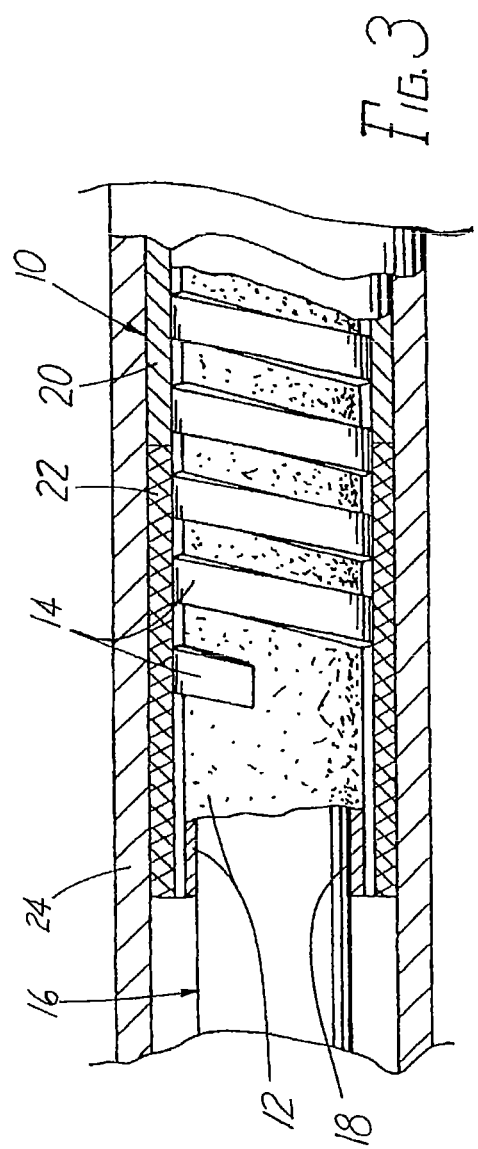
FIG. 3 is an enlarged partial cross-sectional view of the distal tip region of the sheath of the present invention during fabrication thereof.

FIGS. 1 and 2 show an introducer sheath assembly 100 of the prior art, as in U.S. Pat. No. 5,380,304. A dilator 102 extends through a passageway of sheath 104 such that a tapered distal tip 106 of dilator 102 extends beyond the tapered distal end 108 of sheath 104. Sheath 104 also includes a connector valve 110 affixed at its proximal end 112, that includes a silicone disk (not shown) for preventing the backflow of fluids therethrough. Connector valve 110 also includes a side arm 114 to which polyvinyl tube 116 and Luer lock connector 118 are connected for introducing and aspirating fluids therethrough. Tapered distal end 106 of dilator 102 facilitates accessing and dilating a vascular access site over a well-known and commercially available wire guide (not shown). A Luer lock connector hub 120 is attached at the proximal end of the dilator for connection to syringes and other medical apparatus.

Depicted in FIG. 2 is a partially sectioned view of Prior Art introducer sheath 104, with dilator 102 removed from longitudinal sheath passageway 122. Sheath 104 comprises an outer tube 124, an inner tube 126 of polytetrafluoroethylene (PTFE), and a flat wire coil 128 compression fitted around inner tube 126 within outer tube 124. Outer tube 124 is joined to the roughened outer surface 130 of inner tube 126 between the spacings of the coil, in accordance with the disclosure of U.S. Pat. No. 5,380,304, wherein during fabrication a sleeve of heat shrinkable tubing is placed around the outer tube, a mandrel inserted through and beyond inner tube 126, and heat applied until the outer tube melts to flow between the spacings of the wire coil, being urged thereinto by shrinking of the heat shrink sleeve, which is thereafter removed. Pursuant to the patent, a distal tip portion 132 is thermally bonded to a tapered distal end 134 of outer tube 124, and is of the same durometer as outer tube 124, or harder, and has a tapered end that forms tapered distal end 108 of sheath 104. Inner surface 136 of PTFE inner tube 126 is lubricious and slippery to facilitate insertion and withdrawal of dilator 102 and of catheters and the like therethrough. Proximal end 138 of sheath 104 is flared to facilitate retention thereon of valve 110.

Figure 4:
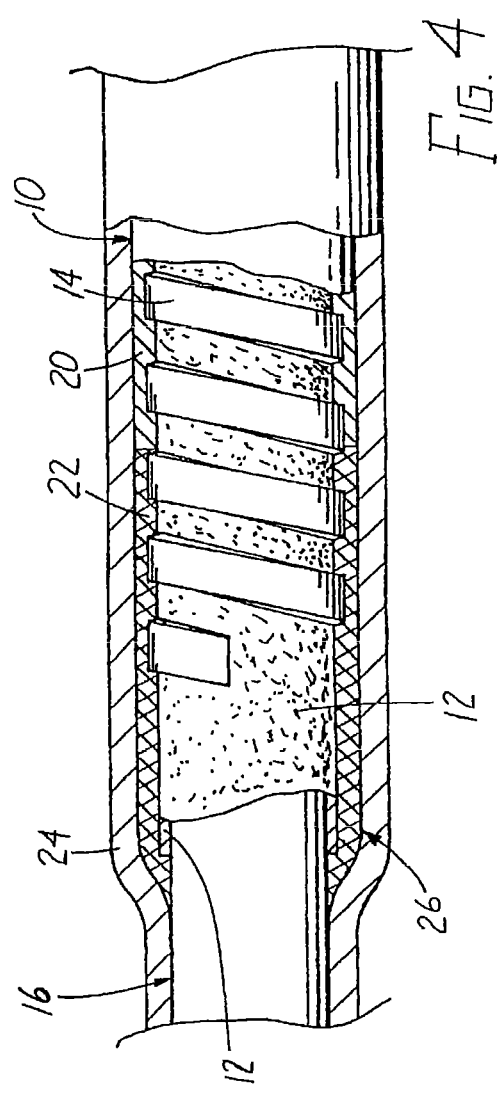
FIG. 4 is a view similar to FIG. 3 after thermal bonding.

In the present invention illustrated in FIGS. 3 to 6, sheath 10 includes an inner tube 12 corresponding to inner tube 126 of FIG. 2, with a roughened outer surface and preferably of PTFE, and flat wire coil 14 wound spirally therearound. A mandrel 16 is inserted through passageway 18 of inner tube 12, and a first length of outer tubing 20 (or proximal outer tubing) is placed over much of the length of the coil-wound inner tube 12, with a selected length of the coil-wound inner tube remaining exposed. First outer tubing length 20 may be of for example nylon having a durometer of between about 50 D and 60 D (Shore D hardness) and may preferably be about 56 to 58 D. However, in certain applications it may be desired for the first outer tubing to have a hardness of up to 80 D.) A second, short length of outer tubing 22 (or distal outer tubing) of nylon having a softer durometer than first tubing length 20, such as between about 35 D and 45 D and preferably about 39 D, is then placed over the exposed length of coil-wound inner tube 12 and abutted against the end of first outer tubing length 20. The exposed length of coil may be about 5 mm to 1 cm or more beyond the distal end of the first outer tube for prevention of kinking at least at the junction of the first and second outer tubing lengths, and the coil may extend if desired for almost the entire length of the second outer tubing, such as for an infusion/drainage catheter with multiple side ports along an extended length.

Regarding the durometer of the second length of outer tubing 22, in applications such as superselective tracking catheters where the leading end must negotiate small, tortuous vessels, the durometer may be selected to be as low as about 10 D for being optimally atraumatic. In other applications such as introducer catheters for placement of stents and various interventional devices where torque transfer and pushability are desired, the durometer of the second tubing length may be selected to be, for example, only about 5 D lower than that of the first length of outer tubing 20, such as about 45 D where the first length 20 is about 50 D.

A length of heat shrinkable sleeve 24 is placed over the entire arrangement, and ends thereof are preheated to shrink at ends of the assembly to hold the first and second lengths against each other. Preferably the first and second lengths of outer tubing 20,22 are distinctly different in color or at least shade, such that abutment can be assured by visual inspection through transparent heat shrinkable sleeve 24.

Upon heating to melt the outer tubing lengths 20,22 to flow between the turns of the coils to bond to inner tube 12 while being compressed by the shrinking of heat shrinkable sleeve 24, a distal tip portion 26 results that is flexible due to the softer durometer of second outer tubing length 22, and that is kink-resistant due to coil 14. After fabrication the heat shrunk sleeve 24 is removed. A taper is then formed adjacent the distal tip of the sheath for a length of about 6 mm, such as by conventional grinding. Optionally, a hydrophilic coating is applied to the outer surface of the sheath.

As seen in FIG. 5, one embodiment of sheath 30 the present invention can have a distal tip region 32 that is linear in form and that is elongate such as about 7 cm, especially suitable for vascular applications involving tortuous paths, the elongate flexible kink-resistant distal tip portion being atraumatic. Also seen is a radiopaque marker band 34 positioned about one-quarter inch from tip 36. In FIG. 6 is seen another embodiment sheath 40 having distal tip region 42 that is formed into an arcuate section by placing the fabricated sheath under elevated temperatures while being constrained in a template of appropriate curvature; for example, a flexible kink-resistant distal tip portion of about 2.5 cm with such curvature is especially suitable for use in entering the renal ostium and eases stress to the renal artery. Preferably, such curvature extends about an angle of about 90°. Where it is desired for the sheath to have a distinct curvature, it would be desirable for the durometer of the second outer tubing length to have a durometer closer to that of the first outer tubing length, such as its durometer being only about 5 D or 10 D lower than that of the first outer tubing length.

The second outer tubing length can have a length of from about 1 cm to about 7 cm and preferably is hydrophilic coated. Preferably a radiopaque marker band, such as of platinum alloy or tungsten or gold, is positioned about the distal end of the coil prior to placement of the outer tubing lengths thereover and thermal bonding, whereafter the marker band becomes embedded within the outer tubing. Additionally, for certain applications it is preferred that the second outer tubing length have a content of radiopaque filler, such as between about 20% and 85%, and preferably about 80%, by weight of tungsten or barium sulphate particles or the like, while the first outer tubing length substantially does not have a radiopaque filler content.

Additionally, it may be desired to provide at least one intermediate outer tubing length between the first and second outer tubing lengths, with a respective durometer between that of the first and second tubing lengths.

The inner tube preferably comprises one continuous tube, but it can be an arrangement formed from two or more tubes fixed in an end-to-end relationship. The use of two or more inner tubes enables the durometer to be reduced in a distal direction in a manner similar to that of the outer tube arrangement which can have two or more outer tubes. The junctions in the inner arrangement would clearly need to be offset from those in the outer arrangement, if there were at least two parts in both the inner and outer tube arrangements.

What is claimed is:

1. A flexible kink-resistant introducer sheath comprising:
an inner tube extending to a distal end;
a wire coil wound around said inner tube extending to an end spaced proximally from said inner tube distal end, said wire coil comprising a plurality of uniformly spaced coil turns, each coil turn being free from crossing by another coil turn;
a first outer tube disposed around said wire coil and said inner tube to a first outer tube distal end spaced proximally from said wire coil distal end such that a distal end portion of said wire coil extends distally beyond the first outer tube distal end;
a radiopaque marker band positioned about the distal end of the coil;
at least a second outer tube disposed around said wire coil and said inner tube therewithin extending distally from said first outer tube distal end and covering said distal end portion of said wire coil and extending beyond said distal end of said inner tube; and
an atraumatic flexible, kink-resistant distal tip;
said first outer tube being of a material having a first durometer of between 50 D and 60 D, and said second outer tube having a second durometer that is softer than said material of said first outer tube and being between 35 D and 45 D;
wherein the second outer tube is polymeric and contains about 80% by weight of radiopaque filler particles;
wherein the first outer tube is substantially free of radiopaque filler; and
wherein the coil extends only partly within the length of the second outer tube.

2. The intravascular sheath according to claim 1, wherein said outer tube and said inner tube are bonded to each other and to said wire coil and to said inner tube between windings of said wire coil.

3. The intravascular sheath according to claim 2, wherein an outwardly facing surface of said inner tube has been roughened to enhance bonding thereto of said first and second outer tubes.

4. The intravascular sheath according to claim 2, wherein said bonding is heat bonding.

5. The intravascular sheath according to claim 1, wherein said second outer tube comprises a material having a durometer of at least 5 D lower than that of the first outer tubing length.

6. The intravascular sheath according to claim 5, wherein said first outer tube comprises a material having a durometer of between 56 D to 58 D.

7. The intravascular sheath according to claim 1, wherein said second outer tube comprises a material having a durometer of about 39 D.

8. The intravascular sheath according to claim 1, wherein said first and second outer tubes are distinctly different in color or shade.

9. The intravascular sheath according to claim 1, wherein said wire coil comprises flat wire.

10. The intravascular sheath according to claim 1, wherein a distal tip region of the sheath is arcuate.

11. The intravascular sheath according to claim 10, wherein said arcuate distal tip region has a length of about 1 cm or more.

12. The intravascular sheath according to claim 10, wherein said arcuate distal tip region extends about an angle of about 90.degree.

13. The intravascular sheath according to claim 1, wherein said wire coil extends for a length of about five millimeters beyond said distal end of said first outer tube.

14. The intravascular sheath according to claim 1, wherein said inner tube is unitarily formed.

15. A flexible kink-resistant introducer sheath comprising:
an inner tube extending to a distal end;
a wire coil wound around said inner tube extending to an end spaced proximally from said inner tube distal end, said wire coil comprising a plurality of uniformly spaced coil turns, each coil turn being free from crossing by another coil turn;
a first outer tube disposed around said wire coil and said inner tube to a first outer tube distal end spaced proximally from said wire coil distal end such that a distal end portion of said wire coil extends distally beyond the first outer tube distal end;
at least a second outer tube disposed around said wire coil and said inner tube therewithin extending distally from said first outer tube distal end and covering said distal end portion of said wire coil and extending beyond said distal end of said inner tube; and
an atraumatic flexible, kink-resistant distal tip;
said first outer tube being of a material having a first durometer of between 50 D and 60 D, and said second outer tube having a second durometer that is softer than said material of said first outer tube and being between 35 D and 45 D;
wherein the second outer tube is polymeric and contains about 80% by weight of radiopaque filler particles;
wherein the first outer tube is substantially free of radiopaque filler; and
wherein the coil extends only partly within the length of the second outer tube.

16. The flexible kink-resistant introducer sheath of claim 15 further comprising at least one intermediate outer tube between the first and second outer tubes and having a respective durometer between that of the first and second outer tubes.

17. The flexible kink-resistant introducer sheath of claim 15 wherein the second outer tube comprises a hydrophilic coating.

18. The flexible kink-resistant introducer sheath of claim 15 wherein the first outer tube has a durometer of only about 5 D higher than the durometer of the second outer tube.

19. The flexible kink-resistant introducer sheath of claim 15 where the coil extends for almost the entire length of the second outer tube.

20. The flexible kink-resistant introducer sheath of claim 15 where the coil does not extend for any length into the atraumatic distal tip.

* * * * *